United States Patent
Hong et al.

(10) Patent No.: US 11,109,820 B2
(45) Date of Patent: Sep. 7, 2021

(54) MAMMOGRAPHY APPARATUS

(71) Applicant: VIEWORKS CO., LTD., Anyang-si (KR)

(72) Inventors: Soon Gil Hong, Cheonan-si (KR); Seok Jong Kim, Namyangju-si (KR); Jung Han Seo, Seoul (KR)

(73) Assignee: VIEWORKS CO., LTD., Anyang-si (KR)

( * ) Notice: Subject to any disclaimer, the term of this patent is extended or adjusted under 35 U.S.C. 154(b) by 23 days.

(21) Appl. No.: 16/754,941

(22) PCT Filed: Oct. 11, 2018

(86) PCT No.: PCT/KR2018/011936
§ 371 (c)(1),
(2) Date: Apr. 9, 2020

(87) PCT Pub. No.: WO2019/074286
PCT Pub. Date: Apr. 18, 2019

(65) Prior Publication Data
US 2020/0253568 A1    Aug. 13, 2020

(30) Foreign Application Priority Data
Oct. 11, 2017    (KR) .......................... 10-2017-0129236

(51) Int. Cl.
*A61B 6/00*    (2006.01)
*A61B 8/08*    (2006.01)
*A61B 6/04*    (2006.01)

(52) U.S. Cl.
CPC .......... *A61B 6/0414* (2013.01); *A61B 6/4441* (2013.01); *A61B 6/502* (2013.01); *A61B 6/54* (2013.01)

(58) Field of Classification Search
CPC ....... A61B 6/032; A61B 6/484; A61B 6/4241; A61B 6/502; A61B 8/0825; A61B 8/4281; A61B 6/0414; A61B 6/4417; A61B 8/403; A61B 90/17; A61B 2017/00557;
(Continued)

(56) References Cited

U.S. PATENT DOCUMENTS

2007/0076844 A1    4/2007    DeFreitas et al.
2018/0368796 A1*   12/2018   Hoernig ............... A61B 8/0825

FOREIGN PATENT DOCUMENTS

JP    2000-255324 A    9/2000
JP    2005-523043 A    8/2005
(Continued)

*Primary Examiner* — Don K Wong
(74) *Attorney, Agent, or Firm* — Rabin & Berdo, P.C.

(57) ABSTRACT

A mammography apparatus according to the present invention includes a mounting part coupled to an elevating part so as to be moved upward or downward and having rail parts, a fastening part inserted into the rail parts and slidably coupled to the mounting part and a sensing part installed on the mounting part and configured to generate an electrical signal by being brought into contact with the fastening part so as to detect information about the fastening part, in which the sensing part includes a contact part installed at an end at an entry side of the fastening part slidably coupled to the mounting part and a recognizing part installed on an inner surface of the mounting part which faces the contact part.

11 Claims, 12 Drawing Sheets

(58) Field of Classification Search
CPC ... A61B 90/11; A61B 10/0233; G01T 1/2985; G01N 2223/419
See application file for complete search history.

(56) References Cited

FOREIGN PATENT DOCUMENTS

JP    2012-024165 A    2/2012
KR    10-1671644 B1    11/2016

* cited by examiner

MAMMOGRAPHY APPARATUS

TECHNICAL FIELD

The present invention relates to a mammography apparatus, and more particularly, to a mammography apparatus capable of improving contact performance and operation reliability of a pressing part configured to press a breast.

BACKGROUND ART

In general, mammography has various advantages of radiography, specifically, X-ray imaging technology and has a unique feature that may minimize the exposure by enlarging images, reducing the number of image capturing processes, increasing the resolution, and adjusting the brightness and contrast ratio, as a result of which the use of mammography is rapidly growing.

The mammography apparatus includes a column disposed perpendicular to a floor and having a columnar shape, a C-arm having a middle part connected to the column so as to be rotatable and movable upward and downward along the column, the C-arm having a C shape or a shape similar thereto as a whole by being bent in an arc shape so that two opposite ends thereof face each other, a generator mounted at one end of the C-arm and configured to emit X rays toward the other end of the C-arm that faces one end, a detector configured to face the generator, and a compression paddle configured to rectilinearly reciprocate between the generator and the detector along an inner surface of the C-arm.

The compression paddle is moved upward or downward by a drive part and directly press a measurement subject, specifically, a breast with a load set based on an electrical signal.

In the related art, a pressure higher than necessary may be applied to the breast when the compression paddle presses the breast placed on a test plate, which pains the subject. In particular, since the size and density of the subject are different for each subject, an appropriate pressure needs to be applied to the subject in accordance with the size and density of the subject. However, the pressure and load to be applied to the subject cannot be appropriately adjusted only by electronic or software control.

This background technology of the present invention is disclosed in Korean Patent Application Laid-Open No. 10-2014-0118443 (published on Oct. 8, 2014) entitled 'Mammography Apparatus and Method of Aligning and Controlling Position of Same'.

DISCLOSURE

Technical Problem

The present invention has been made in an effort to solve the above-mentioned problem and relates to a mammography apparatus in which a fastening part is slidably coupled to a mounting part, such that contact performance and operation reliability of a pressing part may be improved.

Technical Solution

A mammography apparatus according to the present invention includes: a mounting part coupled to an elevating part so as to be moved upward or downward and having rail parts; a fastening part inserted into the rail parts and slidably coupled to the mounting part; and a sensing part installed on the mounting part and configured to generate an electrical signal by being brought into contact with the fastening part so as to detect information about the fastening part, in which the sensing part includes: a contact part installed at an end at an entry side of the fastening part slidably coupled to the mounting part; and a recognizing part installed on an inner surface of the mounting part which faces the contact part.

In the present invention, the mammography apparatus may further include a pressure maintaining part installed on the mounting part and configured to come into contact with the fastening part mounted on the mounting part and to press the fastening part toward the subject.

In the present invention, a first hole portion may be formed in one surface of the mounting part which faces the fastening part, and the pressure maintaining part may penetrate the first hole portion and come into contact with and press the fastening part.

In the present invention, the pressure maintaining part may be a rotatable roller.

In the present invention, a second hole portion may be formed in one surface of the mounting part which faces the fastening part, the mammography apparatus may further include an anti-tilting part disposed to be spaced apart from the pressure maintaining part, and the anti-tilting part may penetrate the second hole portion, come into contact with the fastening part, and press the fastening part toward the subject.

In the present invention, the anti-tilting part may be a rotatable roller.

In the present invention, a fixing hole portion may be formed in one surface of the fastening part which faces the mounting part, the mammography apparatus may further include an anti-withdrawal part configured to reciprocate while penetrating one surface of the mounting part which faces the fastening part, and the anti-withdrawal part may be disposed in the fixing hole portion when the fastening part is coupled to the mounting part.

In the present invention, the anti-withdrawal part may include: an anti-withdrawal main body configured to reciprocate inside the mounting part; and an elastic member coupled to the anti-withdrawal main body, installed inside the mounting part, and configured to elastically support the anti-withdrawal main body against the fastening part.

In the present invention, an end of the anti-withdrawal main body, which is adjacent to the fastening part, may be formed in a hemispheric shape.

In the present invention, a moving hole portion may be formed in the mounting part, and the anti-withdrawal part may further include a lever part coupled to the anti-withdrawal main body and configured to penetrate the moving hole portion and protrude outward from the mounting part.

In the present invention, the rail parts may be formed in groove shapes at both sides based on a central portion in a direction in which the fastening part enters, and the fastening part may have catching portions that protrude outward so as to be caught by the rail parts.

Advantageous Effects

According to the mammography apparatus according to the present invention, the contact part and the recognizing part come into contact with each other as the fastening part is simply and slidably coupled to the mounting part, such that information about the pressing main body part may be recognized.

In addition, as the pressure maintaining part comes into contact with and presses the fastening part, the fastening part is fixed to the mounting part, such that the contact between the contact part and the recognizing part may be maintained.

In addition, since the pressure maintaining part is configured as a rotatable roller, friction between the fastening part and the pressure maintaining part is reduced, such that damage caused by friction may be prevented.

In addition, the anti-tilting part prevents the pressing main body part from being tilted when the pressing main body part presses the subject, and the anti-tilting part maintains the horizontality of the pressing main body part, thereby uniformly maintaining the amount of radiation with which the subject is irradiated.

In addition, since the anti-tilting part is configured as a rotatable roller, friction between the fastening part and the anti-tilting part is reduced, such that damage caused by friction may be prevented.

In addition, the anti-withdrawal part may prevent the fastening part from being withdrawn from the mounting part.

In addition, the elastic member elastically supports the anti-withdrawal main body against the fastening part and presses the anti-withdrawal main body so that the fastening part is tightly attached to the mounting part, thereby preventing the fastening part from being moved in the mounting part.

In addition, the anti-withdrawal part prevents the fastening part from being withdrawn from the mounting part, such that the contact force between the contact part and the recognizing part and operation reliability may be improved.

DESCRIPTION OF MAIN REFERENCE NUMERALS OF DRAWINGS

Figure 1:
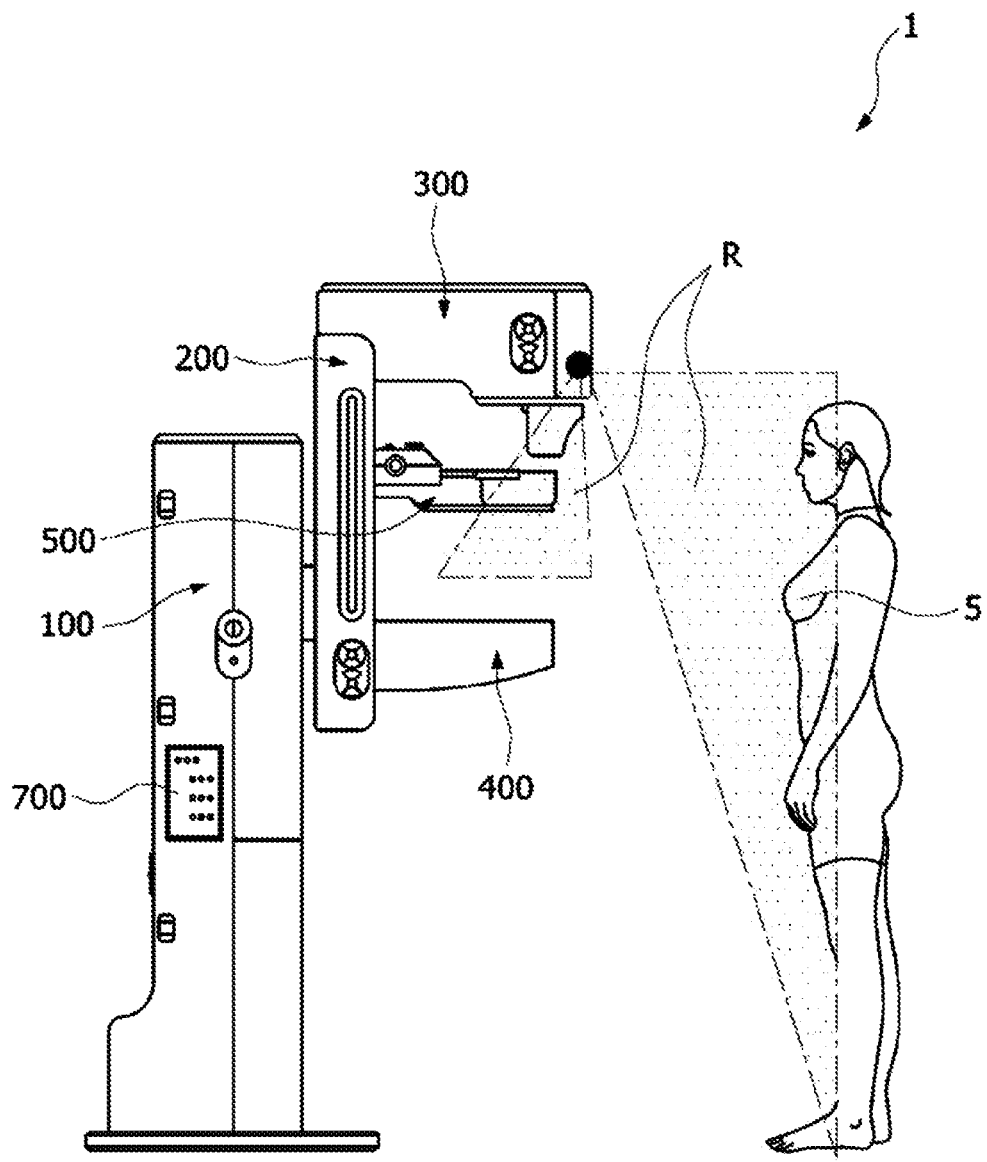
FIG. 1 is a side view illustrating a mammography apparatus according to an exemplary embodiment of the present invention.

1: Mammography apparatus
R: Radiation beam
L: Lubricant
5: Subject
100: Main body part
200: Measurement arm part
210: Moving frame part
220: Drive part
230: Driving shaft part
240: Loader part
241: Fixing part
243: Rotary part
250: Power transmission part
260: Transfer part
261: First transfer part
263: Second transfer part
265: Connecting part
270: Elevating part
280: Load adjusting part
290: Safety ensuring part
295: Measurement part
300: Irradiation part
400: Image capturing part
500: Pressing part
510: Mounting part
511: Rail part
513: First hole portion
515: Second hole portion
517: Moving hole portion
520: Fastening part
521: Frame part
522: Fixing hole portion
523: Catching portion
525: Pressing main body part
530: Sensing part
531: Contact part
533: Recognizing part
540: Pressure maintaining part
550: Anti-tilting part
560: Anti-withdrawal part
561: Anti-withdrawal main body
562: Coupling groove portion
563: Elastic member
565: Lever part
600: Control part
700: Display part

[Best Mode]

Hereinafter, an exemplary embodiment of a mammography apparatus according to the present invention will be described with reference to the accompanying drawings. Here, thicknesses of lines illustrated in the drawings, sizes of constituent elements, or the like may be exaggerated for clarity and convenience of description.

In addition, the terms used below are defined considering the functions in the present invention and may vary depending on the intention of a user or an operator or a usual practice. Therefore, the definition of the terms should be made based on the entire contents of the present invention.

Figure 2:
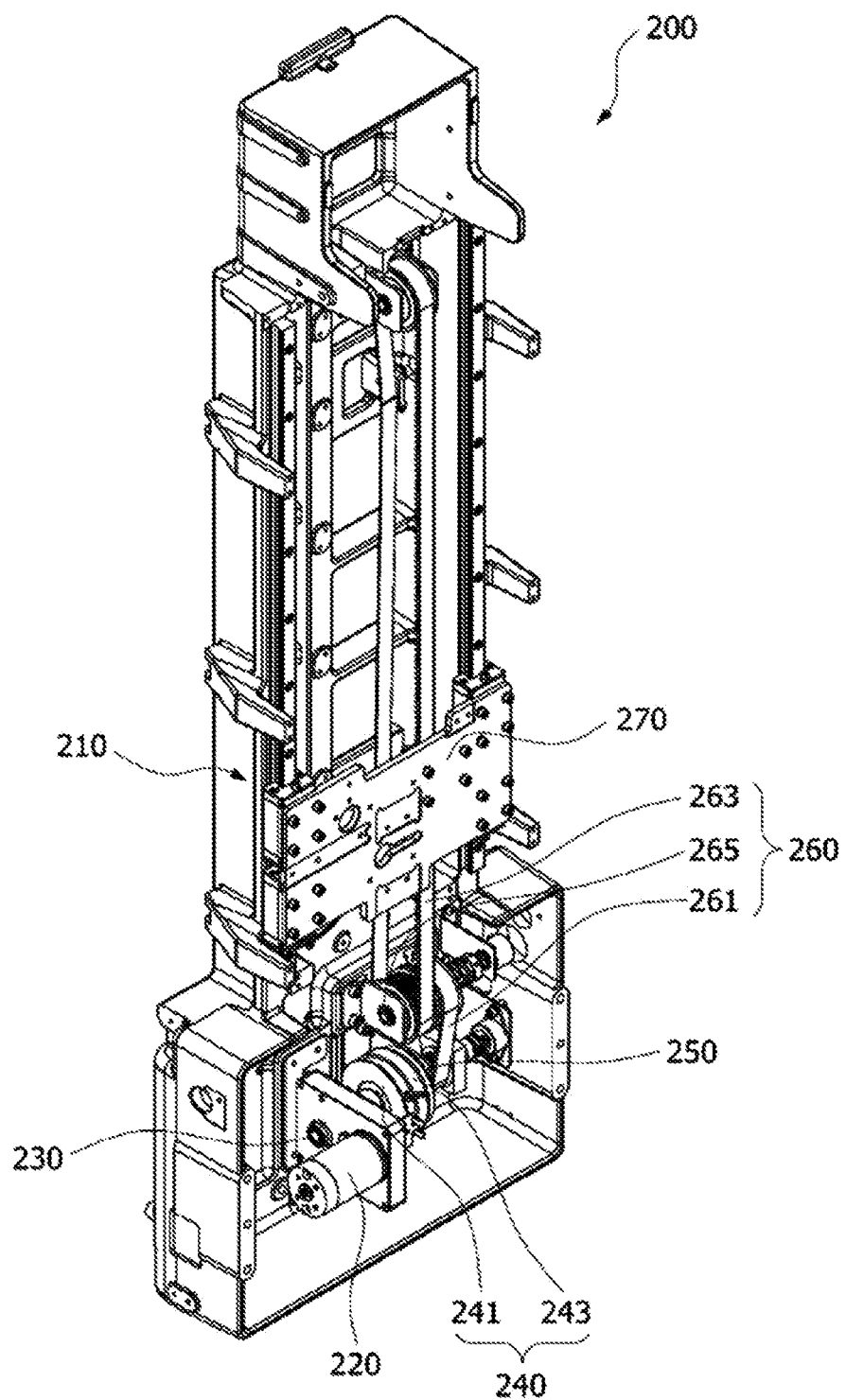
FIG. 2 is a perspective view illustrating a main body part according to the exemplary embodiment of the present invention.
Figure 3:
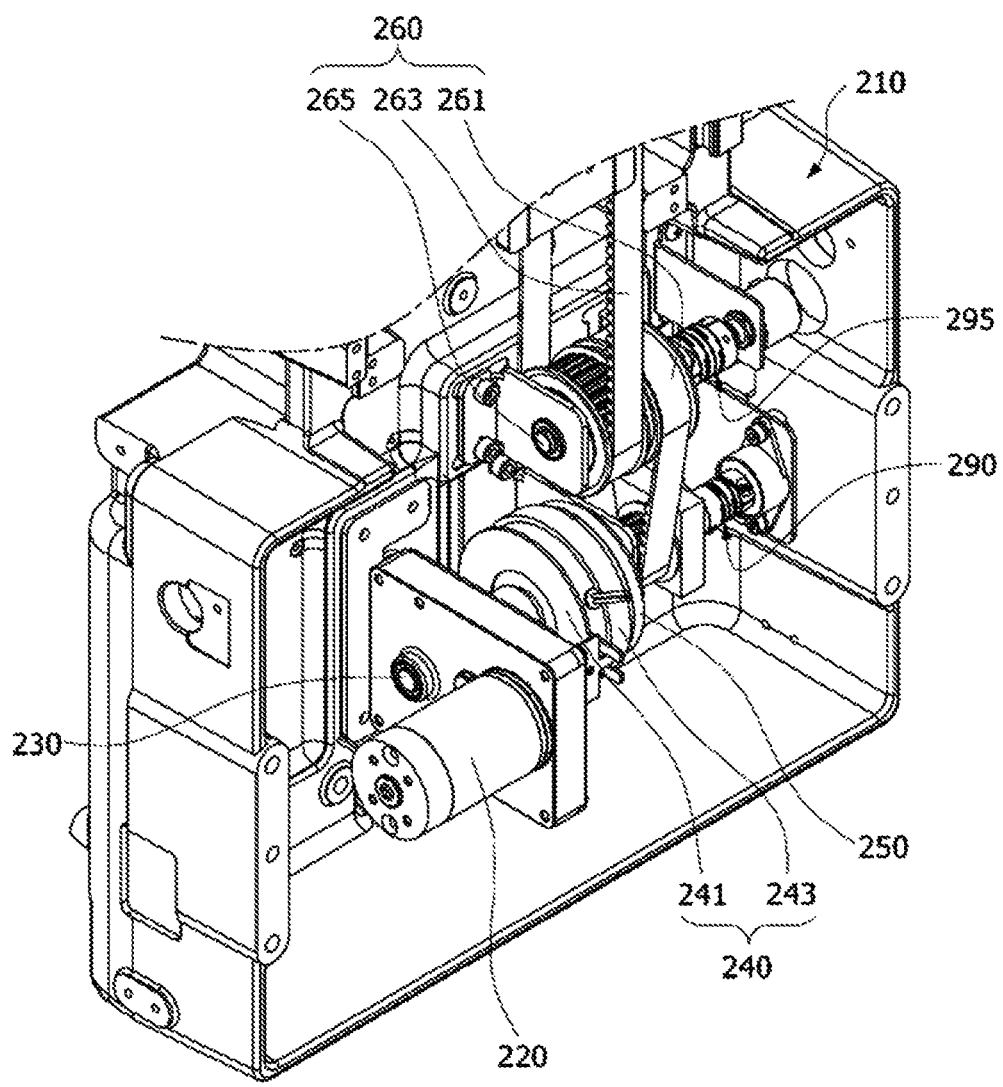
FIG. 3 is an enlarged view illustrating a drive part according to the exemplary embodiment of the present invention.
Figure 4:
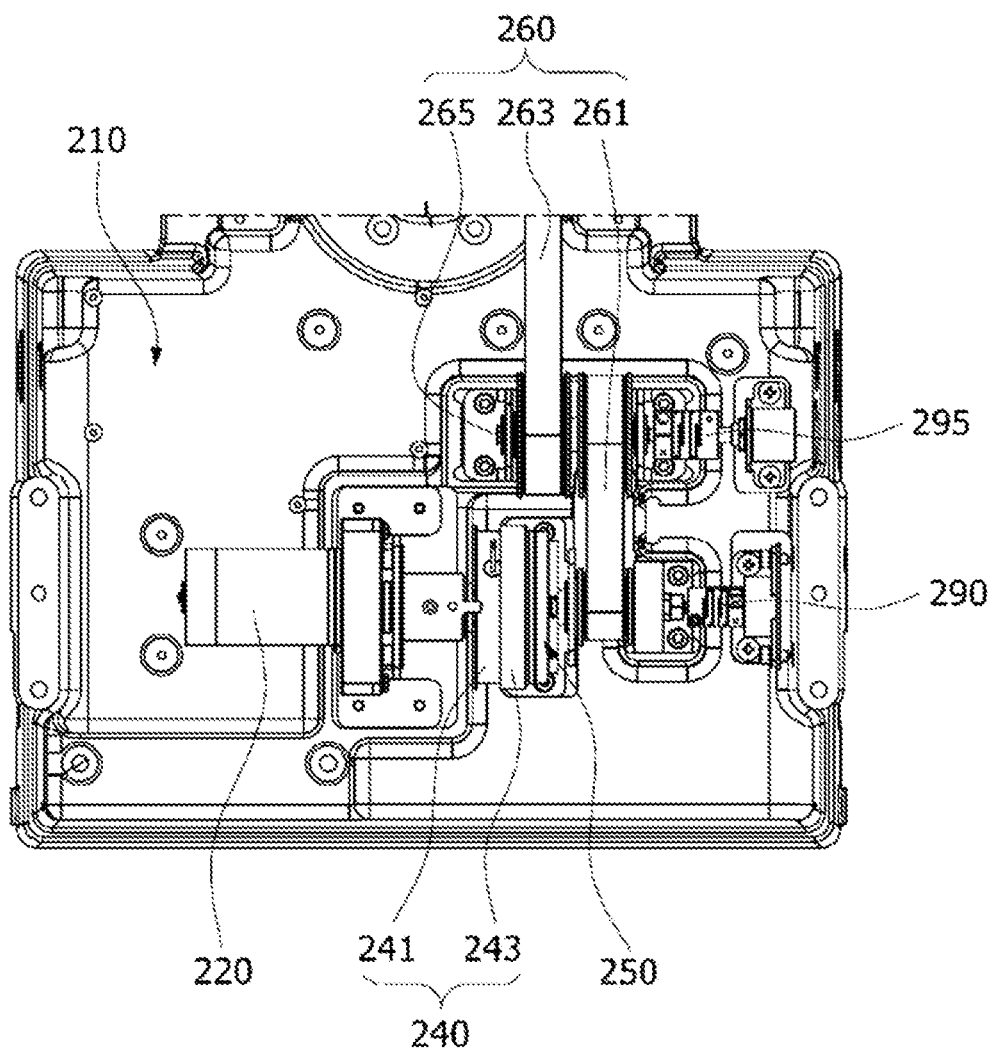
FIG. 4 is a side view illustrating a power transmission part according to the exemplary embodiment of the present invention.
Figure 5:
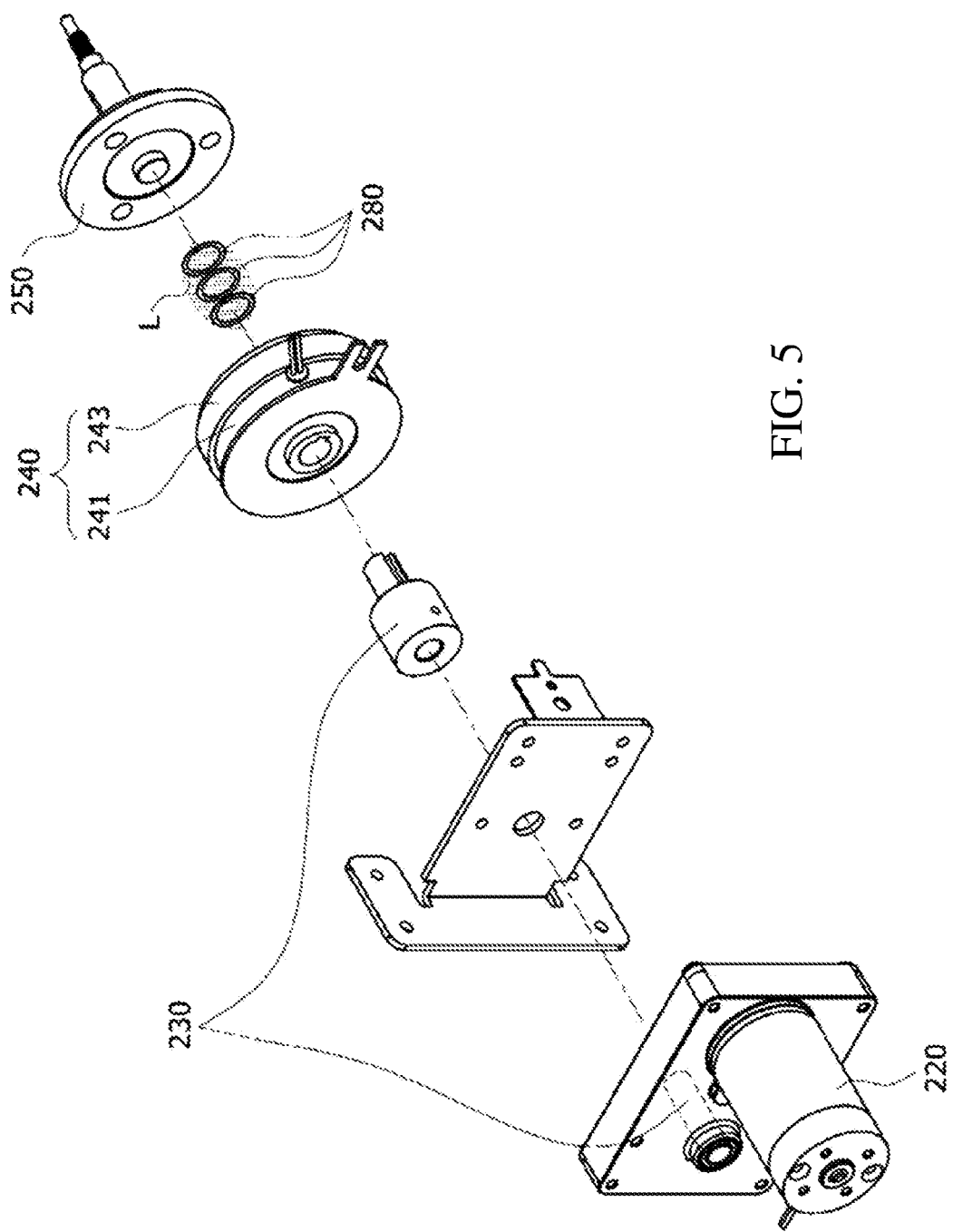
FIG. 5 is an exploded perspective view illustrating a load adjusting part according to the exemplary embodiment of the present invention.
Figure 6:
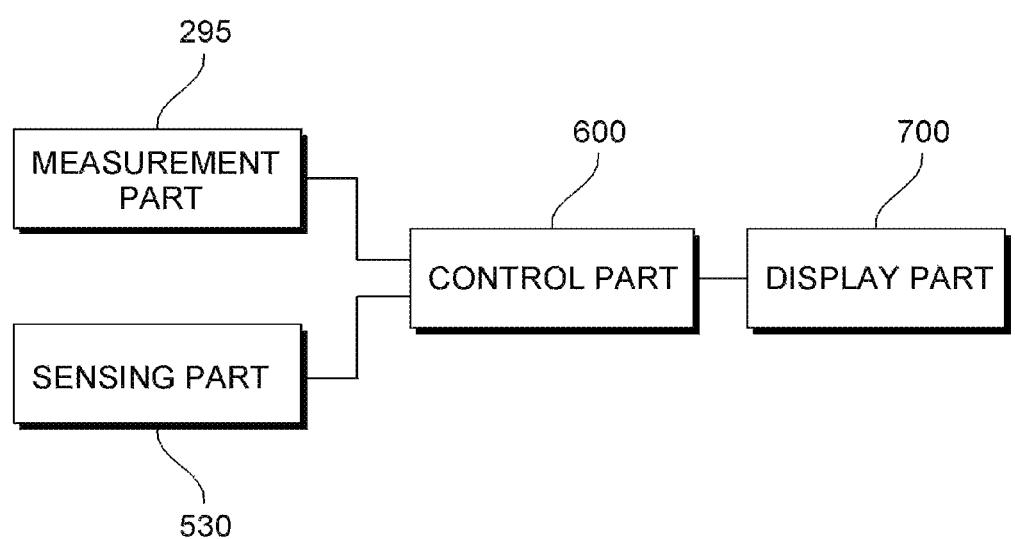
FIG. 6 is a block configuration view illustrating a measurement part according to the exemplary embodiment of the present invention.
Figure 7:
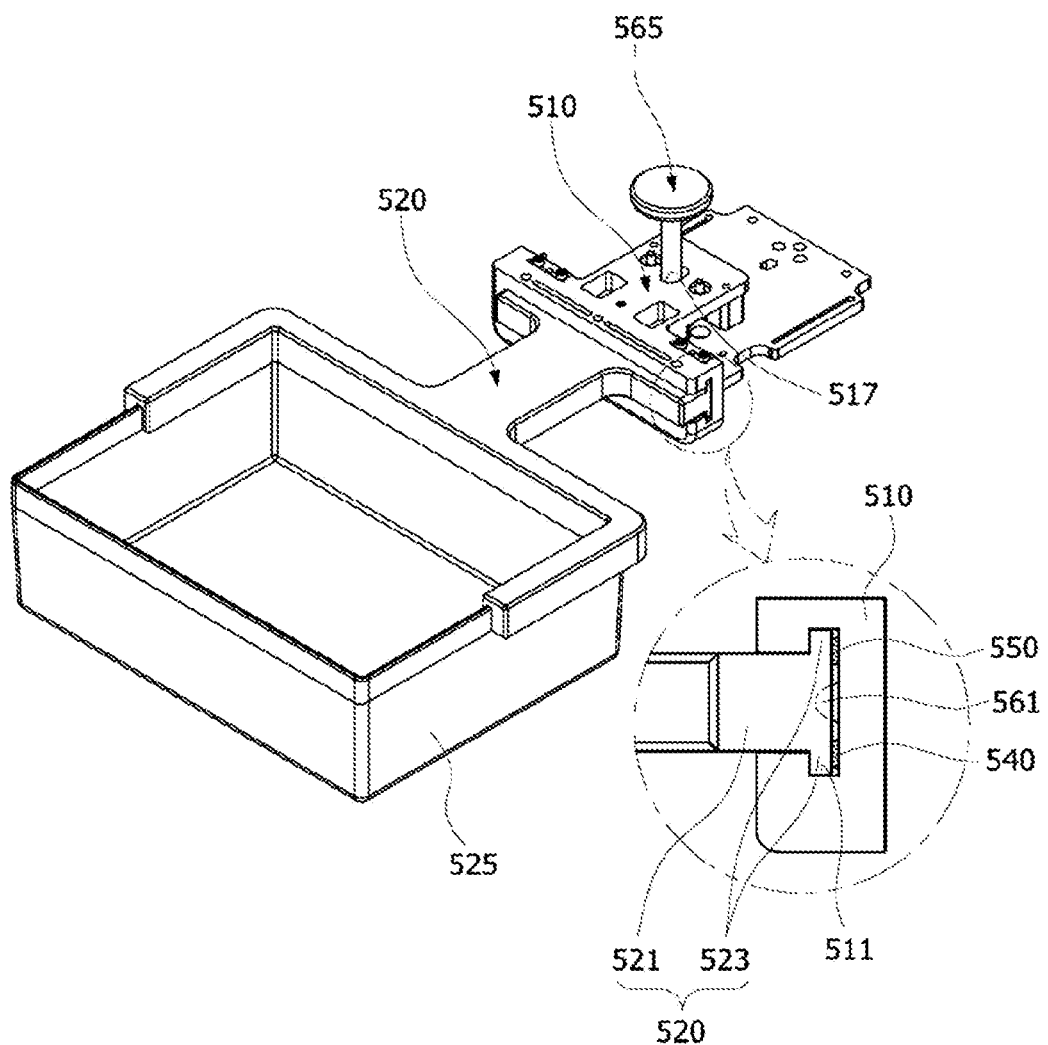
FIG. 7 is a perspective view illustrating a mounting part according to the exemplary embodiment of the present invention.
Figure 8:
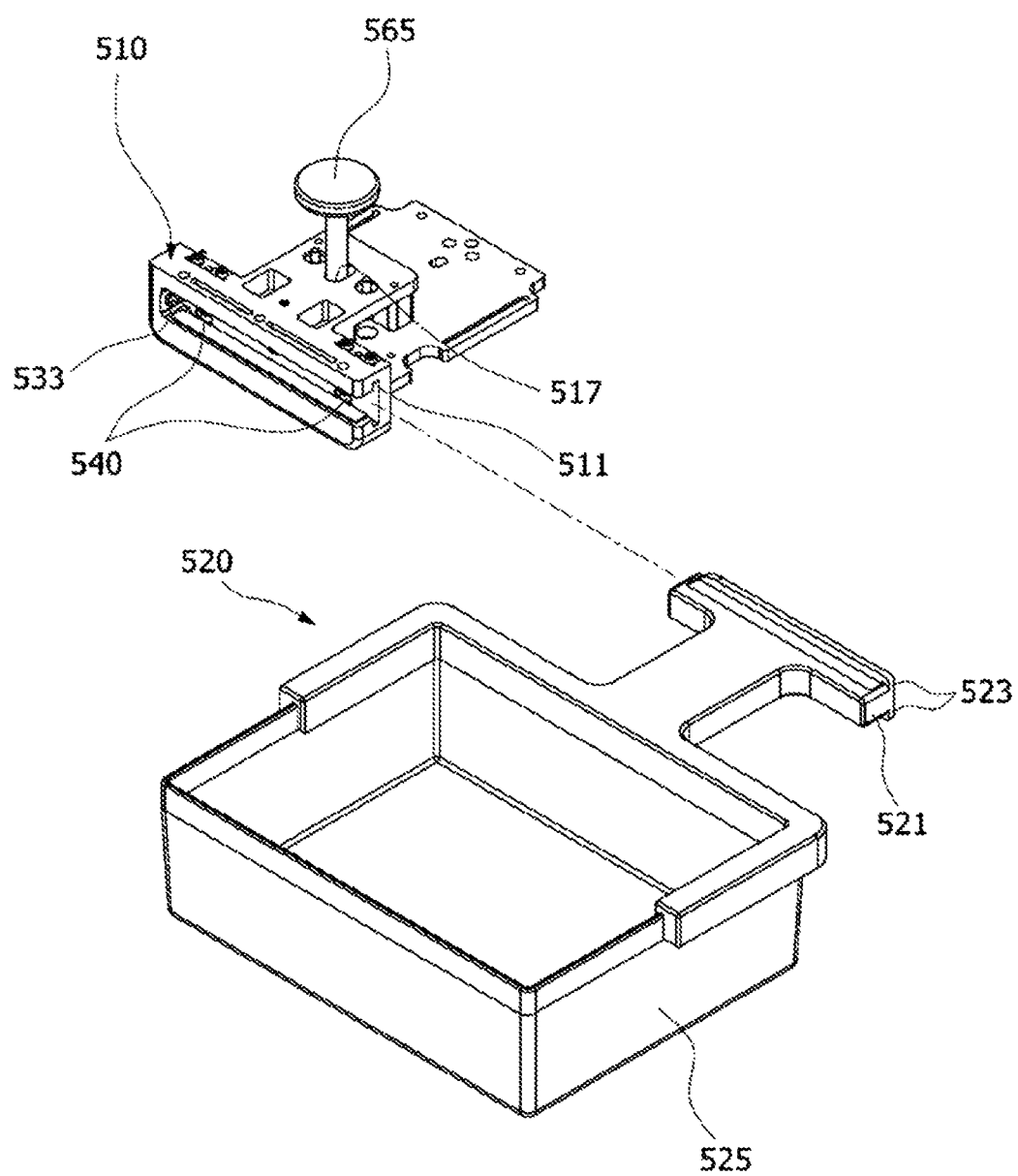
FIG. 8 is an exploded view illustrating the mounting part according to the exemplary embodiment of the present invention.
Figure 9:
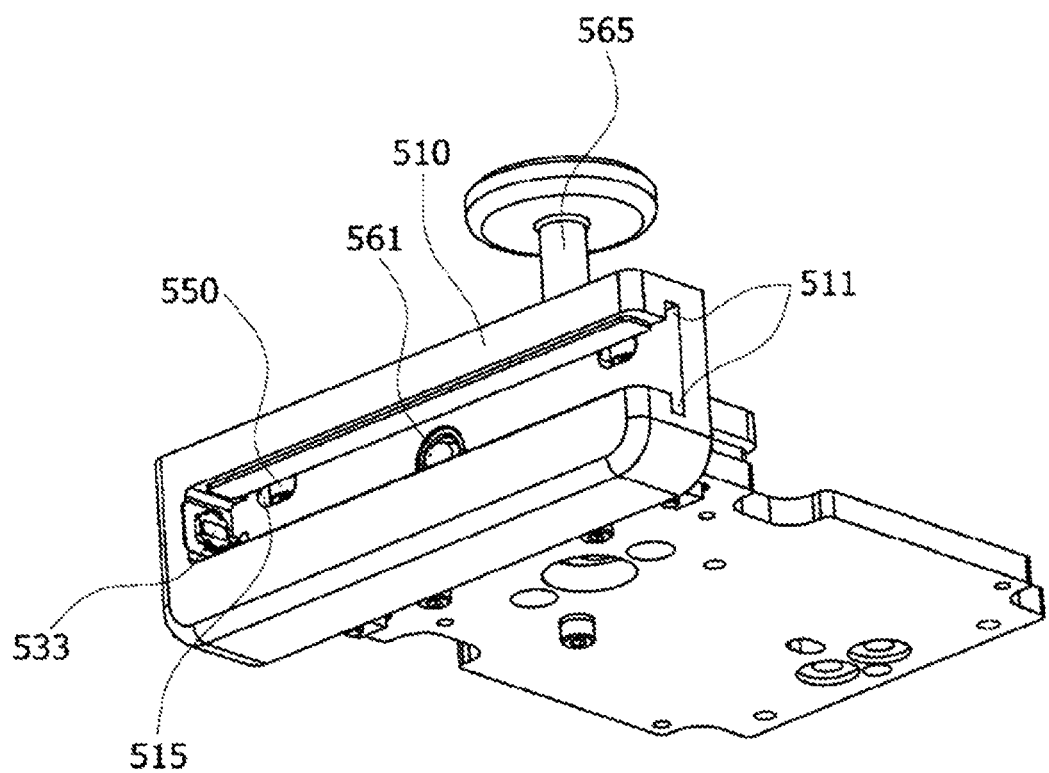
FIG. 9 is a bottom perspective view illustrating the mounting part according to the exemplary embodiment of the present invention.
Figure 10:
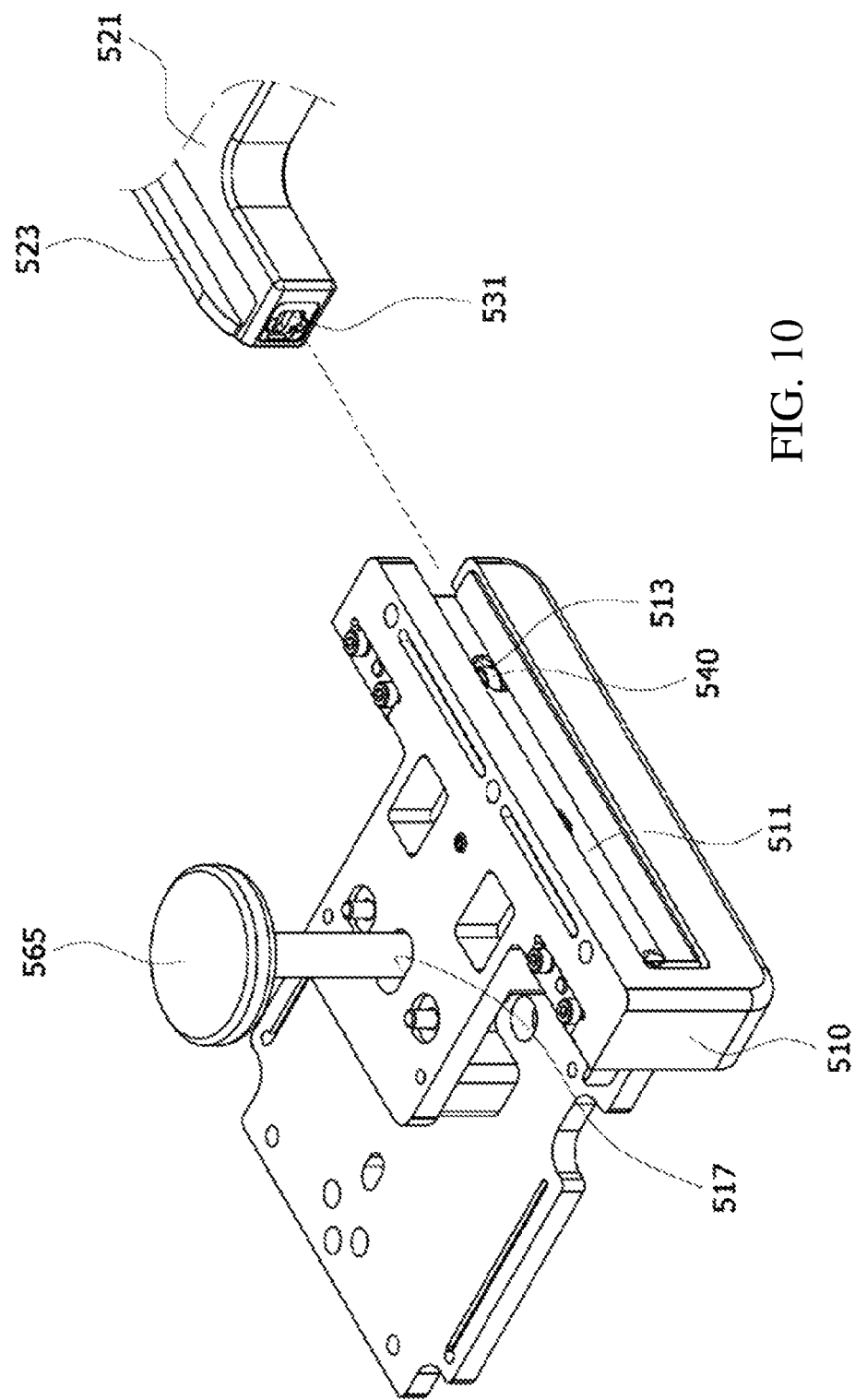
FIG. 10 is a perspective view illustrating the mounting part according to the exemplary embodiment of the present invention.
Figure 11:
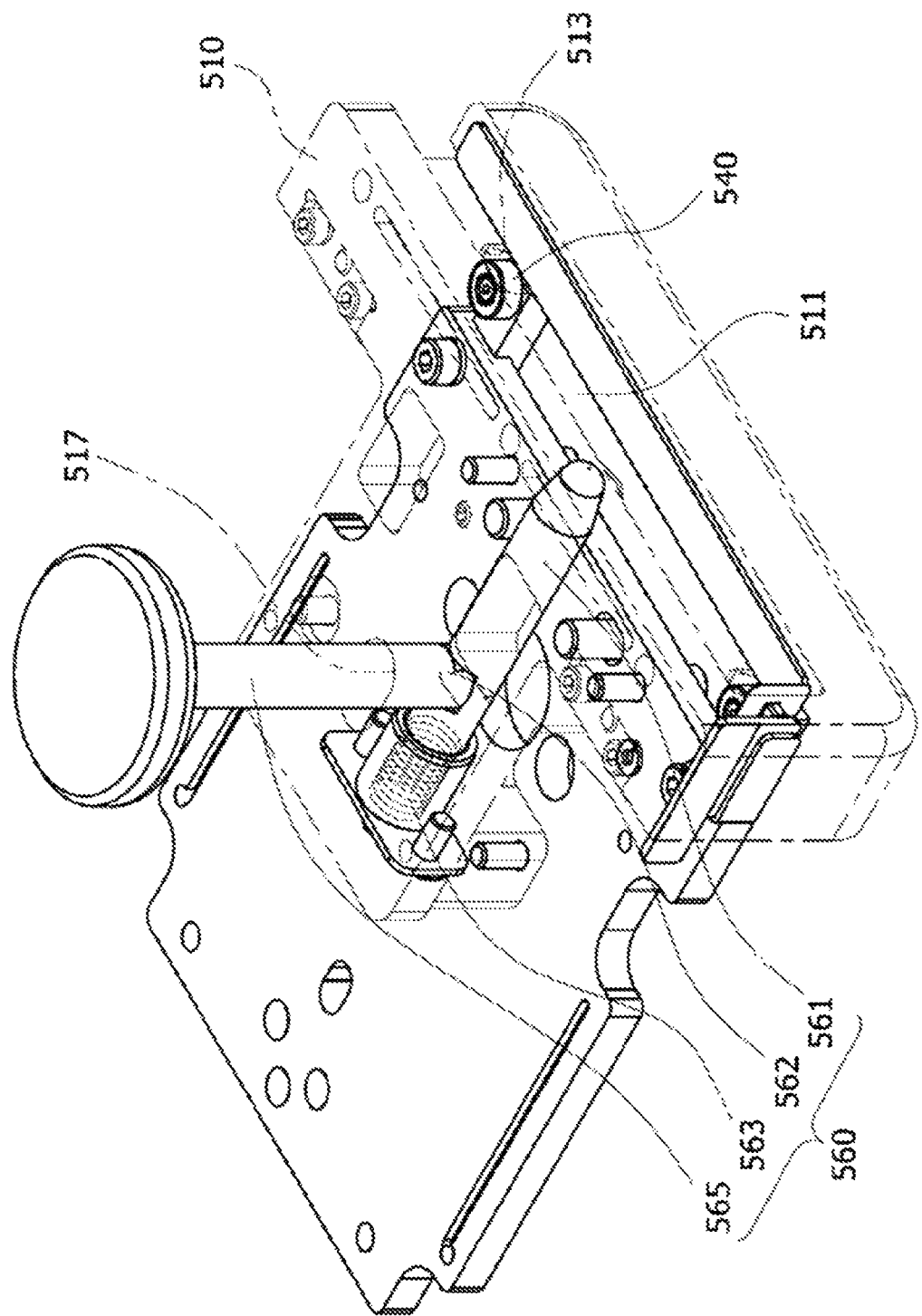
FIG. 11 is a perspective view illustrating an anti-withdrawal part according to the exemplary embodiment of the present invention.
Figure 12:
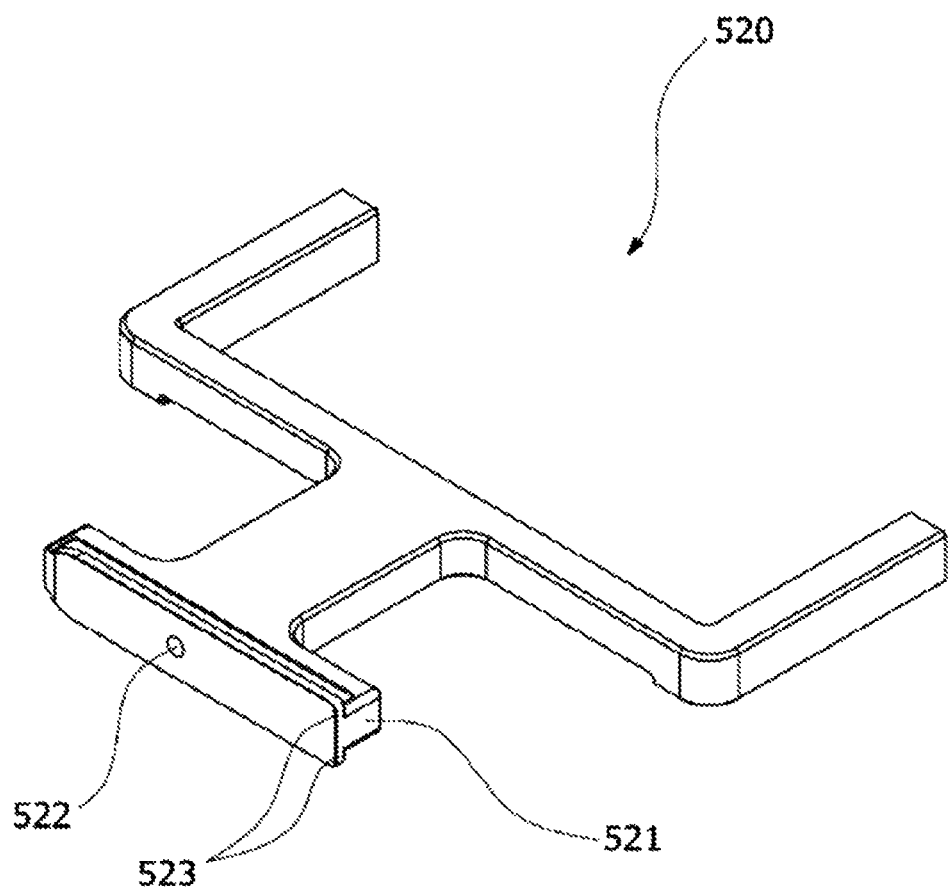
FIG. 12 is a perspective view illustrating a frame part according to the exemplary embodiment of the present invention.

FIG. 1 is a side view illustrating a mammography apparatus according to an exemplary embodiment of the present invention. FIG. 2 is a perspective view illustrating a main body part according to the exemplary embodiment of the present invention. FIG. 3 is an enlarged view illustrating a drive part according to the exemplary embodiment of the present invention. FIG. 4 is a side view illustrating a power transmission part according to the exemplary embodiment of the present invention. FIG. 5 is an exploded perspective view illustrating a load adjusting part according to the exemplary embodiment of the present invention. FIG. 6 is a block configuration view illustrating a measurement part according to the exemplary embodiment of the present invention. FIG. 7 is a perspective view illustrating a mounting part according to the exemplary embodiment of the present invention. FIG. 8 is an exploded view illustrating the mounting part according to the exemplary embodiment of the present invention. FIG. 9 is a bottom perspective view illustrating the mounting part according to the exemplary embodiment of the present invention. FIG. 10 is a perspective view illustrating the mounting part according to the exemplary embodiment of the present invention. FIG. 11 is a perspective view illustrating an anti-withdrawal part according to the exemplary embodiment of the present invention. FIG. 12 is a perspective view illustrating a frame part according to the exemplary embodiment of the present invention.

Referring to FIGS. 1 to 6, a mammography apparatus 1 according to an exemplary embodiment of the present invention includes a main body part 100, a measurement arm part 200, an irradiation part 300, an image capturing part 400, a pressing part 500, a control part 600, and a display part 700.

Referring to FIG. 1, the main body part 100 is disposed perpendicular to a floor and has a column shape. The main body part 100 is fixedly installed on the floor, and the measurement arm part 200 to be described below is installed on the main body part 100 so as to be rotatable and movable upward and downward.

Referring to FIGS. 1 and 2, the measurement arm part 200 according to the exemplary embodiment of the present invention is coupled to the main body part 100 and installed on the main body part 100 so as to be rotatable and movable upward and downward.

Therefore, when measuring a subject 5, specifically, a breast, an image capturing process may be performed while pressing the breast in an up-down direction (based on FIG. 1) or pressing the breast in a left-right direction when viewed from a front side of the subject 5.

The measurement arm part 200 according to the exemplary embodiment of the present invention includes a moving frame part 210, a drive part 220, a driving shaft part 230, a loader part 240, a power transmission part 250, a transfer part 260, an elevating part 270, a load adjusting part 280, a safety ensuring part 290, and a measurement part 295.

The moving frame part 210 is installed inside the measurement arm part 200 and provides an upward/downward movement path (in the up-down direction based on FIG. 2) of the elevating part 270 to be described below.

On the moving frame part 210, the drive part 220, the driving shaft part 230, the loader part 240, the power transmission part 250, the transfer part 260, the elevating part 270, the load adjusting part 280, the safety ensuring part 290, and the measurement part 295, which will be described below, are installed.

Referring to FIGS. 2 to 4, the drive part 220 according to the exemplary embodiment of the present invention is configured to generate power, and the drive part 220 generates rotational power by using a motor by being supplied with electric power from the outside.

The power is generated by the drive part 220 and transmitted to the transfer part 260 by the power transmission part 250, such that the elevating part 270 is moved upward or downward.

The driving shaft part 230 according to the exemplary embodiment of the present invention is rotated by being supplied with the power from the drive part 220, and the driving shaft part 230 is disposed inside the loader part 240 to be described below. As such, the loader part 240 is rotated as the driving shaft part 230 is rotated.

The loader part 240 includes a fixed part 241 coupled to the drive part 220, and a rotary part 243 rotatably coupled to the fixed part 241.

Referring to FIGS. 2 to 4, the power transmission part 250 according to the exemplary embodiment of the present invention is selectively brought in the contact with the loader part 240 by electromagnetic force. The power transmission part 250 comes into contact with the loader part 240 when the electromagnetic force is generated, while the power transmission part 250 is spaced apart from the loader part 240 when no electromagnetic force is generated.

Therefore, when the electromagnetic force is generated, the power transmission part 250 comes into contact with the loader part 240 to generate magnetic force, such that the power transmission part 250 is rotated, and the rotational power transmitted from the drive part 220 is transmitted to the transfer part 260.

The transfer part 260 and the power transmission part 250 are rotated together about the same center axis. The power transmission part 250 and the transfer part 260 are coupled to each other by being splined together or by means of a key. When the power transmission part 250 comes into contact with the loader part 240, the power transmission part 250 and the transfer part 260 are rotated together by being supplied with power from the drive part 220.

Therefore, the power from the drive part 220 is transmitted to the transfer part 260, and the elevating part 270 is moved upward or downward on the measurement arm part 200.

Referring to FIGS. 2 to 4, the transfer part 260 according to the exemplary embodiment of the present invention is operated by being coupled to the power transmission part 250 and includes a first transfer part 261, a second transfer part 263, and a connecting part 265.

The first transfer part 261 according to the exemplary embodiment of the present invention is connected to the power transmission part 250 and rotated about the same center axis as the power transmission part 250 in conjunction with the rotation of the power transmission part 250. The first transfer part 261 is rotated like an endless track and, specifically, may be configured in the form of a belt.

The second transfer part 263 according to the exemplary embodiment of the present invention is coupled to the elevating part 270, such that the elevating part 270 is moved upward or downward in the up-down direction (based on FIG. 1) on the measurement arm part 200 in accordance with the movement of the second transfer part 263.

The second transfer part 263 is rotated about the same rotation center axis as the first transfer part 261 in conjunction with the rotation of the first transfer part 261, and the rotation center axis is disposed at one end of the second transfer part 263. The second transfer part 263 is rotated like an endless track and, specifically, may be configured in the form of a belt.

Referring to FIGS. 3 and 5, the connecting part 265 according to the exemplary embodiment of the present invention is configured to connect the first transfer part 261 and the second transfer part 263 and transmit the power from the first transfer part 261 to the second transfer part 263.

The connecting part 265 has a plurality of gear parts (denoted by no reference numeral), specifically, a first gear part and a second gear part, which are rotated by being engaged with the first transfer part 261 and the second transfer part 263, respectively.

The gear parts of the connecting part 265 according to the exemplary embodiment of the present invention, which are coupled to the first transfer part 261 and the second transfer part 263, respectively, have the same diameter.

However, the present invention is not limited thereto, and various modifications may be made such that the first gear part, which is coupled to the first transfer part 261, and the second gear part, which is coupled to the second transfer part 263, have different diameters or gear teeth so as to increase or decrease a speed.

Referring to FIGS. 1 and 2, the elevating part 270 according to the exemplary embodiment of the present invention is coupled to the transfer part 260 and configured to be moved upward and downward, and the pressing part 500 to be described below is mounted on the elevating part 270.

The elevating part 270 is coupled to the transfer part 260, specifically, to the second transfer part 263 that is moved upward or downward by being supplied with power from the drive part 220. As the transfer part 260 is moved, the elevating part 270 may be moved upward or downward on the measurement arm part 200.

Referring to FIG. 5, the load adjusting part 280 according to the exemplary embodiment of the present invention are installed between the loader part 240 and the power transmission part 250 and adjust intervals between the power transmission part 250 and the loader part 240, specifically, the rotary part 243.

The plurality of load adjusting parts 280 may be provided and in contact with one another, such that the magnetic force between the loader part 240 and the power transmission part 250 is increased or decreased.

Specifically, the magnetic force between the loader part 240 and the power transmission part 250 is decreased as the number of load adjusting parts 280 is increased, and the magnetic force between the loader part 240 and the power transmission part 250 is increased as the number of load adjusting parts 280 is decreased.

The load adjusting part 280 is formed in a ring shape and surrounds the center shaft of the power transmission part 250. The load adjusting part 280 is installed between the power transmission part 250 and the loader part 240.

Therefore, when the electromagnetic force is generated, the power transmission part 250 is moved toward the loader part 240 (to the left based on FIG. 5), and the magnetic force is generated, such that the rotational power of the drive part 220 is transmitted to the transfer part 260.

The power transmission part 250 is moved along the center axis, and a movement distance of the power transmission part 250 varies depending on a magnitude of a load that the pressing part 500 to be described below applies to the subject 5. Specifically, as the load is increased, the power transmission part 250 is moved, by a higher electromagnetic force, toward the loader part 240, specifically, toward the rotary part 243.

The load adjusting part 280 is in friction contact with the loader part 240, specifically, the rotary part 243 and the power transmission part 250, respectively, such that an interval between the power transmission part 250 and the loader part 240 is prevented from becoming below a predetermined distance at which a slip occurs.

Further, the movement distance of the power transmission part 250 toward the loader part 240 is set to correspond to a required pressing load of the pressing part 500, and the power transmission part 250 is prevented from being moved toward the loader part 240 beyond the movement distance.

The load adjusting part 280 prevents the power transmission part 250 from being moved toward the loader part 240 beyond the set movement distance due to software errors or the like and prevent the subject 5 from being pressed with a load exceeding the set load due to a high electromagnetic force.

Referring to FIG. 5, as the number of load adjusting parts 280 between the power transmission part 250 and the loader part 240 is increased, a maximum movement distance of the power transmission part 250 toward the loader part 240 is decreased. Therefore, when maximally moving the power transmission part 250, the subject 5 may be prevented from being pressed with a load exceeding the pressing load of the pressing part 500 made by the electromagnetic force corresponding to the interval between the power transmission part 250 and the loader part 240.

Referring to FIG. 5, a lubricant L is applied onto the load adjusting part 280 according to the exemplary embodiment of the present invention. The lubricant L may be grease or the like.

Since the lubricant L is applied onto the load adjusting part 280, the occurrence of noise caused by the contact with the power transmission part 250 and the loader part 240 is prevented when the power transmission part 250 is moved toward the loader part 240, specifically, toward the rotary part 243.

Referring to FIGS. 2 to 4, the safety ensuring part 290 according to the exemplary embodiment of the present invention is coupled to an end at the other side (the right side based on FIG. 4) opposite to one side (the left side based on the FIG. 4) of the power transmission part 250 that faces the loader part 240. The safety ensuring part 290 prevents the pressing part 500 from falling toward the subject 5 when the mammography apparatus 1 is suddenly stopped due to a power failure or the like.

Specifically, the safety ensuring part 290 is coupled to a center shaft of the power transmission part 250 and rotated together with the power transmission part 250.

When the safety ensuring part 290 is rotated, by the movement of the transfer part 260, specifically, of the second transfer part 263, in one direction (clock or counterclockwise) in which the pressing part 500 is moved upward, a valve part (not illustrated in the drawings) in the safety ensuring part 290 is opened and the lubricant L is inputted so that the safety ensuring part 290 is smoothly rotated.

When the safety ensuring part 290 is rotated, by the movement of the transfer part 260, specifically, of the second transfer part 263, in the other direction (counterclockwise or clockwise) in which the pressing part 500 is moved downward, the valve part is closed to block the input of the lubricant L so that the resistance against the downward (based on FIG. 2) movement of the pressing part 500 is increased.

Referring to FIGS. 2 to 4 and 6, the measurement part 295 according to the exemplary embodiment of the present invention is coupled to the connecting part 265 and detects a position of the elevating part 270 by a current transfer method.

The measurement part 295 outputs, as a voltage, the amount of change in resistance values and is electrically connected to the control part 600. The measurement part 295 is connected to the connecting part 265 and measures, as a voltage output, the rotation displacement of the connecting part 265 that rotates in conjunction with the second transfer part 263, and the measurement part 295 transfers the measured value to the control part 600.

The measured value transferred to the control part 600 is converted, by a series of calculation processes, into a value of a current position of the elevating part 270 in accordance with the rotation displacement of the connecting part 265, and the converted value is transferred to the display part 700.

Referring to FIGS. 1 and 6, the display part 700 according to the exemplary embodiment of the present invention is installed on the main body part 100 and receives an electrical signal from the control part 600, such that the position of the elevating part 270, specifically, the position of the pressing part 500, which is coupled to the elevating part 270 and moved, is converted into visual information and then outputted.

Referring to FIG. 1, the irradiation part 300 according to the exemplary embodiment of the present invention is coupled at an upper side (based on FIG. 1) of the measurement arm part 200 and emits radiation beam R toward the image capturing part 400 installed at a lower side (based on FIG. 1) of the measurement arm part 200.

In the present invention, X-rays are used as the radiation, but the present invention is not limited thereto, and various modifications may be made in which gamma rays and the like, which may be used for medical purposes, are used.

Referring to FIG. 1, the image capturing part 400 according to the exemplary embodiment of the present invention is coupled to the measurement arm part 200 and installed at the other side opposite to one end of the measurement arm part 200 at which the irradiation part 300 is installed. Further, the image capturing part 400 is installed to face the irradiation part 300. The subject 5 is disposed on the image capturing part 400, and the radiation beam R emitted from the irradiation part 300 penetrate the pressing part 500 and reach the subject 5.

Referring to FIGS. 1 and 7 to 12, the pressing part 500 according to the exemplary embodiment of the present invention is coupled to the elevating part 270 and moved upward or downward (vertically moved based on FIG. 1) on the measurement arm part 200.

The pressing part 500 includes a mounting part 510, a fastening part 520, a sensing part 530, a pressure maintaining part 540, an anti-tilting part 550, and an anti-withdrawal part 560.

Referring to FIGS. 8, 9, and 10, the mounting part 510 according to the exemplary embodiment of the present invention is coupled to the elevating part 270 and moved upward or downward, and the mounting part 510 has rail parts 511.

The rail parts 511 are formed in groove shapes at both sides (upper and lower sides based on FIG. 8) based on a central portion in a direction in which the fastening part 520 to be described below enters (in a direction from the right to the left based on FIG. 8).

Referring to FIG. 9, one side (the right side based on FIG. 9) of the mounting part 510 is opened so that the fastening part 520 to be described below may enter the mounting part 510. A cross section of the right side (based on FIG. 9) of the mounting part 510 is formed in a shape made by cutting a predetermined left section out of a 'ㄷ' shape.

Therefore, the fastening part 520 is caught by the rail parts 511, thereby preventing the fastening part 520 from being withdrawn from the mounting part 510. The rail parts 511 are caught by catching portions 523 that protrude outward (based on FIG. 8) from the fastening part 520, specifically, from a frame part 521.

Referring to FIG. 10, a first hole portion 513 is formed in one surface of the mounting part 510 which faces the fastening part 520. The pressure maintaining part 540 to be described below passes through the first hole portion 513 and comes into contact with and presses the fastening part 520 mounted on the mounting part 510.

Referring to FIG. 9, a second hole portion 515 is formed in one surface of the mounting part 510 which faces the fastening part 520. The second hole portion 515 is formed at an upper side (based on FIG. 9) of the first hole portion 513. The anti-tilting part 550 to be described below passes through the second hole portion 515 and comes into contact with and presses the fastening part 520 mounted on the mounting part 510.

Referring to FIGS. 8 and 10, the fastening part 520 according to the exemplary embodiment of the present invention is inserted into the rail parts 511 and slidably coupled to the mounting part 510. The fastening part 520 includes the frame part 521 and a pressing main body part 525.

The pressing main body part 525 to be described below is mounted on the frame part 521. In the present invention, the pressing main body part 525 is slidably coupled to the frame part 521, but the present invention is not limited thereto, and various modifications may be made in which the pressing main body part 525 is coupled to the frame part 521 by a fastening member such as a bolt.

A fixing hole portion 522 is formed in one surface of the frame part 521 according to the exemplary embodiment of the present invention which faces the mounting part 510.

Therefore, when the fastening part 520, specifically, the frame part 521 is fastened to the mounting part 510, the anti-withdrawal main body 561 to be described below is disposed inside the fixing hole portion 522, thereby preventing the frame part 521 from being withdrawn from the mounting part 510.

The catching portions 523 protrude outward from the upper and lower sides (based on FIG. 8) of the frame part 521, and the catching portions 523 is caught by the rail parts 511 formed on the mounting part 510 and each having a groove shape.

Therefore, the fastening part 520, specifically, the frame part 521 may be prevented from being withdrawn from the mounting part 510.

The pressing main body part 525 according to the exemplary embodiment of the present invention is coupled to the frame part 521 and presses the subject 5 disposed on the image capturing part 400.

In the present invention, the pressing main body part 525 has a rectangular parallelepiped shape opened at an upper side thereof, but the present invention is not limited thereto, and the pressing main body part 525 may be modified to have various shapes in accordance with a shape of the breast, which is the subject 5.

The sensing part 530 according to the exemplary embodiment of the present invention is installed on the mounting part 510 and generates an electrical signal when the sensing part 530 comes into contact with the fastening part 520. The sensing part 530 detects the type of fastening part 520, specifically, the type of pressing main body part 525. The sensing part 530 includes a contact part 531 and a recognizing part 533.

Referring to FIG. 10, the contact part 531 according to the exemplary embodiment of the present invention is installed at an end at an entry side (the left side based on FIG. 10) of the fastening part 520 slidably coupled to the mounting part 510.

Referring to FIG. 9, the recognizing part 533 according to the exemplary embodiment of the present invention is installed on an inner surface of the mounting part 510 which faces the contact part 531. An electrical signal is generated as the recognizing part 533 comes into contact with the contact part 531.

The contact part 531 varies depending on the type of fastening part 520, specifically, the type of pressing main body part 525, and a resistance value, which is measured when the contact part 531 and the recognizing part 533 come into contact with each other, varies depending on the type of fastening part 520, specifically, on the type of pressing main body part 525.

Therefore, it is possible to recognize the type of pressing main body part 525 fastened to the mounting part 510 by reading the resistance value in accordance with the corresponding pressing main body part 525.

The electrical signal, which is generated by the contact between the contact part 531 and the recognizing part 533, is transmitted to the control part 600, and the control part 600 transmits the electrical signal to the display part 700, thereby displaying the type of pressing main body part 525 currently mounted on the mounting part 510 as visual or auditory information.

Referring to FIGS. 7 and 10, the pressure maintaining part 540 according to the exemplary embodiment of the present invention is installed on the mounting part 510 and comes into contact with and presses the fastening part 520, which is mounted on the mounting part 510, toward the subject 5.

Specifically, the pressure maintaining part 540 penetrates the first hole portion 513 and comes into contact with and presses the fastening part 520. The pressure maintaining part 540 further protrudes toward the fastening part 520 mounted on the mounting part 510 than one surface of the mounting part 510 in which the first hole portion 513 is formed.

Therefore, the fastening part 520 is prevented from vibrating due to an interval between the mounting part 510 and the fastening part 520, and the sensing part 530 is prevented from being released, specifically, the contact part 531 and the recognizing part 533 are prevented from being separated from each other due to the vibration of the fastening part 520.

The pressure maintaining part 540 according to the exemplary embodiment of the present invention is configured as a rotatable roller, such that frictional force, which is generated when the fastening part 520 is slidably coupled to the mounting part 510, is reduced, and thus damage caused by friction may be prevented.

The plurality of pressure maintaining parts 540 according to the exemplary embodiment of the present invention may be provided and disposed at both sides (the left and right sides based on FIG. 10) based on the central portion of the mounting part 510.

Therefore, the pressing force applied to the fastening part 520 coupled to the mounting part 510 may be increased, such that the fastening part 520 is prevented from vibrating with a coupling section in the mounting part 510.

Referring to FIGS. 7 and 9, the anti-tilting part 550 according to the exemplary embodiment of the present invention is disposed to be spaced apart from the pressure maintaining part 540. The anti-tilting part 550 penetrates the second hole portion 515 formed in one surface of the mounting part 510 which faces the fastening part 520, and then the anti-tilting part 550 comes into contact with and presses the fastening part 520.

Specifically, the anti-tilting part 550 penetrates the second hole portion 515 formed in the mounting part 510 and comes into contact with and presses the fastening part 520. The anti-tilting part 550 further protrudes toward the fastening part 520 than one surface of the mounting part 510 in which the second hole portion 515 is formed.

Therefore, when the pressing main body part 525 presses the subject 5, specifically, the breast, the pressing main body part 525 is prevented from being tilted due to the shape of the breast, and the horizontality of the pressing main body part 525 is maintained, thereby uniformly maintaining the amount of radiation with which the breast is irradiated.

The anti-tilting part 550 according to the exemplary embodiment of the present invention is configured as a rotatable roller, such that frictional force, which is generated when the fastening part 520 is slidably coupled to the mounting part 510, is reduced, and thus damage caused by friction may be prevented.

The plurality of anti-tilting parts 550 according to the exemplary embodiment of the present invention may be provided and disposed at both sides (the left and right sides based on FIG. 9) based on the central portion of the mounting part 510.

Therefore, the pressing force applied to the fastening part 520 coupled to the mounting part 510 is increased, such that the fastening part 520 is prevented from being tilted in the mounting part 510 in accordance with the shape of the breast, and the horizontality of the fastening part 520 is maintained.

Referring to FIG. 11, the anti-withdrawal part 560 according to the exemplary embodiment of the present invention reciprocates while penetrating one surface of the mounting part 510 which faces the fastening part 520. The anti-withdrawal part 560 is disposed in the fixing hole portion 522 formed in one surface of the fastening part 520 when the fastening part 520 is slidably coupled to the mounting part 510.

The anti-withdrawal part 560 includes an anti-withdrawal main body 561, an elastic member 563, and a lever part 565. Referring to FIG. 11, the anti-withdrawal main body 561 according to the exemplary embodiment of the present invention reciprocates inside the mounting part 510.

In the present invention, the anti-withdrawal main body 561 is formed in a cylindrical shape, but the present invention is not limited thereto, and various modifications may be made in which the anti-withdrawal main body 561 is formed in a polygonal column shape so as to be movable inside the mounting part 510.

The elastic member 563 according to the exemplary embodiment of the present invention is coupled to the anti-withdrawal main body 561 and installed inside the mounting part 510. The elastic member 563 elastically supports the anti-withdrawal main body 561 against the fastening part 520.

In the present invention, the elastic member 563 is configured as a spring, but the present invention is not limited thereto, and various modifications may be made in which the elastic member 563 is configured as a cylinder.

The lever part 565 according to the exemplary embodiment of the present invention is coupled to the anti-withdrawal main body 561. The lever part 565 penetrates a moving hole portion 517 formed in an upper surface (based on FIG. 10) of the mounting part 510, and then the lever part 565 protrudes outward (upward based on FIG. 10) from the mounting part 510.

The lever part 565 is orthogonal to an axial direction of the anti-withdrawal main body 561 and may be coupled to the anti-withdrawal main body 561. A coupling groove portion 562 is formed in the anti-withdrawal main body 561, and the lever part 565 is fastened to the coupling groove portion 562 by thread engagement or the like.

Hereinafter, an operational principle and an effect of the mammography apparatus 1 according to the exemplary embodiment of the present invention will be described.

Referring to FIG. 1, the main body part 100 is installed perpendicular to the floor surface, the measurement arm part 200 is installed on the main body part 100, and the measurement arm part 200 is movable upward or downward so as to be adapted to a height of the subject 5 or rotatable to be adapted to an angle at which the subject 5, specifically, the breast is measured.

The image capturing part 400, on which the subject 5, specifically, the breast is disposed, is coupled at the lower side (based on FIG. 1) of the measurement arm part 200, and the irradiation part 300 is coupled at the upper side (based on FIG. 1) of the measurement arm part 200. The irradiation part 300 emits the radiation beam R such as X-ray beam toward the subject 5.

The pressing part 500, which is moved upward or downward on the measurement arm part 200, is installed between the image capturing part 400 and the irradiation part 300. The pressing part 500 is fixedly coupled to the elevating part 270. The elevating part 270 is moved upward or downward (in the up-down direction based on FIG. 2) on the moving frame part 210 installed in the measurement arm part 200, and a principle of the upward/downward movement of the elevating part 270 is as follows.

The loader part 240 is disposed outside the driving shaft part 230 which is rotated by being supplied with power from the drive part 220, and the power transmission part 250 is brought into contact with the loader part 240 by the electromagnetic force generated by receiving the electrical signal from the outside.

The loader part 240, specifically, the rotary part 243 is rotated in conjunction with the rotation of the driving shaft part 230, and the power transmission part 250 is moved toward the loader part 240 (to the left based on FIG. 5) by the electromagnetic force. The power transmission part 250 comes into contact with the loader part 240, receives power from the loader part 240, and transmits the power to the transfer part 260.

The load adjusting part 280 is installed between the loader part 240 and the power transmission part 250 and adjusts the interval between the loader part 240 and the power transmission part 250.

Specifically, when no electromagnetic force is generated, the loader part 240, specifically, the rotary part 243 and the power transmission part 250 are spaced apart from each other, and no power is transmitted from the drive part 220 to the transfer part 260.

In this case, when power is supplied from the outside and electromagnetic force is generated, the power transmission part 250 is moved toward the loader part 240 and transmits the power by means of friction.

As the electromagnetic force is increased, the higher power is transmitted. The power is proportional to the load applied to the subject 5 by the elevating part 270 coupled to the transfer part 260. The power transmission part 250 is moved toward the loader part 240 by a predetermined distance in accordance with a set load value.

The power transmission part 250 and the loader part 240 are spaced apart from each other at a predetermined interval even though the set load value is reached. If a malfunction in software or a program occurs, the power transmission part 250 is moved toward the loader part 240 further than the movement distance corresponding to the set load value, and the pressing part 500 presses the subject 5 with a load higher than the load value set by the higher electromagnetic force.

The load adjusting parts 280 installed between the loader part 240 and the power transmission part 250 allow a slip to occur between the loader part 240 and the power transmission part 250, thereby preventing the power transmission part 250 from being moved toward the loader part 240 beyond the movement distance corresponding to the set load value.

Further, the load adjusting parts 280 prevent the pressing part 500 from pressing the subject 5 with a load exceeding the set load value.

Referring to FIG. 5, the plurality of load adjusting parts 280 may be provided and disposed to correspond to the load value of the pressing part 500 that presses the subject 5.

Specifically, the power to be transmitted and the load of the pressing part 500 for pressing the subject 5 are increased as the interval between the loader part 240 and the power transmission part 250 is decreased. Therefore, as the plurality of load adjusting parts 280 is installed, a total thickness of the load adjusting parts 280 is increased, and a distance by which the power transmission part 250 may be moved toward the loader part 240 is decreased, thereby reducing a maximum pressing load value.

The load adjusting parts 280 may prevent the power transmission part 250 from being moved toward the drive part 220 beyond a load value set by program errors and prevent the subject 5 from being injured due to an excessive load.

Referring to FIGS. 3 and 4, the safety ensuring part 290 is connected to the center shaft of the power transmission part 250 and rotated together with the power transmission part 250. The safety ensuring part 290 prevents the load from being increased as the pressing part 500 for pressing the subject 5 is moved downward when the mammography apparatus 1 is stopped due to an unexpected accident such as a power failure.

Specifically, the safety ensuring part 290 may have, therein, the valve part that discharges the lubricant L used to allow the center shaft of the power transmission part 250 to smoothly rotate. When the pressing part 500 is moved upward (based on FIG. 2), the valve part is opened to allow the center shaft of the power transmission part 250 to smoothly rotate. When the pressing part 500 is moved downward (based on FIG. 2), the valve part is closed to produce resistive force against the rotation.

Therefore, when the mammography apparatus 1 is stopped, the user may smoothly move the pressing part 500 upward, and the pressing part 500 may be prevented from falling suddenly.

Referring to FIGS. 3, 4, and 6, the measurement part 295 is coupled to the connecting part 265 and detects the position of the elevating part 270 by a current transfer method, and the measurement part 295 outputs, as a voltage, the rotation displacement of the transfer part 260, specifically, of the second transfer part 260.

Referring to FIGS. 1 and 6, the outputted voltage is transferred to the control part 600 and converted, by a series of calculation processes, into a value of a current position of the elevating part 270 in accordance with the rotation displacement of the connecting part 265, and the converted value is transferred to the display part 700.

Therefore, this configuration enables the user, specifically, the measurer to recognize where the elevating part 270 and the pressing part 500 coupled to the elevating part 270 are currently positioned, thereby improving operation reliability of the mammography apparatus 1.

Referring to FIGS. 2 and 7, the mounting part 510 is coupled to the elevating part 270 and moved upward or downward on the measurement arm part 200, specifically, on the moving frame part 210.

The rail parts 511 are formed on the mounting part 510, and the fastening part 520 is slidably coupled to the mounting part 510. The fastening part 520 includes the frame part 521 and the pressing main body part 525, and the pressing main body part 525 is mounted on the frame part 521 and configured to press the subject 5, specifically, the breast.

Referring to FIGS. 9 and 10, the sensing part 530 includes the contact part 531 and the recognizing part 533. The fastening part 520 is coupled to be slidable along the rail parts 511 at the lateral side of the mounting part 510, and the contact part 531 installed at the end at the entry side of the fastening part 520 comes into contact with the recognizing part 533 installed on the inner surface of the mounting part 510 which faces the contact part 531.

Therefore, in order to allow the user to measure the subject 5, the contact part 531 and the recognizing part 533 come into contact with each other as the fastening part 520 is simply and slidably coupled to the mounting part 510, and as a result, the type of fastening part 520, specifically, the type of pressing main body part 525 may be recognized.

Referring to FIG. 10, the pressure maintaining part 540 penetrates the first hole portion 513 formed in the mounting part 510 and then protrudes outward from the mounting part 510. The pressure maintaining part 540 is configured as a roller and rotatably comes into friction contact with the fastening part 520 slidably coupled to the mounting part 510.

As the pressure maintaining part 540 comes into contact with the fastening part 520 and presses the fastening part 520 toward the subject 5, the fastening part 520 is tightly fixed to the mounting part 510, such that the contact part 531 and the recognizing part 533 are prevented from being spaced apart from each other, and thus operation reliability of the mammography apparatus 1 is improved.

Referring to FIG. 9, the anti-tilting part 550 penetrates the second hole portion 515 formed in the mounting part 510 and protrudes outward from the mounting part 510. The anti-tilting part 550 is configured as a roller and prevents the pressing main body part 525 from being tilted due to the shape of the breast when the pressing main body part 525 presses the subject 5, specifically, the breast, such that the horizontality of the pressing main body part 525 is maintained.

Since the horizontality of the pressing main body part 525 is maintained, the radiation may be uniformly applied to the subject 5, that is, the breast.

Referring to FIG. 11, an end of the anti-withdrawal part 560, which is adjacent to the fastening part 520, is formed in a hemispheric shape, such that when the fastening part 520 is slidably coupled to the mounting part 510, the anti-withdrawal part 560 is slipped and disposed inside the fixing hole portion 522 formed in the fastening part 520, specifically, in the frame part 521.

The elastic member 563 elastically supports the anti-withdrawal main body 561 against the fastening part 520 and presses the anti-withdrawal main body 561 so that the fastening part 520 is tightly attached to the mounting part 510, such that the fastening part 520 may be prevented from being moved in the mounting part 510, and the contact force may be maintained in the sensing part 530, specifically, between the contact part 531 and the recognizing part 533.

In order to separate the fastening part 520 from the mounting part 510 or replace the fastening part 520, the elastic member 563 is compressed by pulling the lever part 565 toward a rear side opposite to the side of the fastening part 520, and the anti-withdrawal main body 561 is moved to the inside of the mounting part 510 from the fastening part 520, such that the fastening part 520 may be separated from the mounting part 510.

While the present invention has been described with reference to the exemplary embodiment depicted in the drawings, the exemplary embodiment is described just for illustration, and those skilled in the art will understand that various modifications of the exemplary embodiment and any other exemplary embodiment equivalent thereto are available. Accordingly, the technical protection scope of the present invention should be determined by the appended claims.

The invention claimed is:

1. A mammography apparatus comprising:
  a mounting part coupled to an elevating part so as to be moved upward or downward and having rail parts;
  a fastening part inserted into the rail parts and slidably coupled to the mounting part; and
  a sensing part installed on the mounting part and configured to generate an electrical signal by being brought into contact with the fastening part so as to detect information about the fastening part,
  wherein the sensing part comprises:
  a contact part installed at an end at an entry side of the fastening part slidably coupled to the mounting part; and
  a recognizing part installed on an inner surface of the mounting part which faces the contact part.

2. The mammography apparatus of claim 1, further comprising:
  a pressure maintaining part installed on the mounting part and configured to come into contact with the fastening part mounted on the mounting part and to press the fastening part toward the subject.

3. The mammography apparatus of claim 2, wherein a first hole portion is formed in one surface of the mounting part which faces the fastening part, and the pressure maintaining part penetrates the first hole portion and comes into contact with and presses the fastening part.

4. The mammography apparatus of claim 3, wherein the pressure maintaining part is a rotatable roller.

5. The mammography apparatus of claim 3, wherein a second hole portion is formed in one surface of the mounting part which faces the fastening part, the mammography apparatus further comprises an anti-tilting part disposed to be spaced apart from the pressure maintaining part, and the anti-tilting part penetrates the second hole portion, comes into contact with the fastening part, and presses the fastening part toward the subject.

6. The mammography apparatus of claim 5, wherein the anti-tilting part is a rotatable roller.

7. The mammography apparatus of claim 1, wherein a fixing hole portion is formed in one surface of the fastening part which faces the mounting part, and
  wherein the mammography apparatus further comprises an anti-withdrawal part configured to reciprocate while penetrating one surface of the mounting part which faces the fastening part, and the anti-withdrawal part is disposed in the fixing hole portion when the fastening part is coupled to the mounting part.

8. The mammography apparatus of claim 7, wherein the anti-withdrawal part comprises:
   an anti-withdrawal main body configured to reciprocate inside the mounting part; and
   an elastic member coupled to the anti-withdrawal main body, installed inside the mounting part, and configured to elastically support the anti-withdrawal main body against the fastening part.

9. The mammography apparatus of claim 8, wherein an end of the anti-withdrawal main body, which is adjacent to the fastening part, is formed in a hemispheric shape.

10. The mammography apparatus of claim 9, wherein a moving hole portion is formed in the mounting part, and the anti-withdrawal part further comprises a lever part coupled to the anti-withdrawal main body and configured to penetrate the moving hole portion and protrude outward from the mounting part.

11. The mammography apparatus of claim 1, wherein the rail parts are formed in groove shapes at both sides based on a central portion in a direction in which the fastening part enters, and the fastening part has catching portions that protrude outward so as to be caught by the rail parts.

* * * * *